(12) United States Patent
Sugiura et al.

(10) Patent No.: US 7,771,738 B2
(45) Date of Patent: Aug. 10, 2010

(54) SILVER-BASED INORGANIC ANTIMICROBIAL AGENT AND ANTIMICROBIAL PRODUCT

(75) Inventors: Koji Sugiura, Aichi (JP); Yasuharu Ono, Aichi (JP)

(73) Assignee: Toagosei Co., Ltd., Tokyo (JP)

( * ) Notice: Subject to any disclaimer, the term of this patent is extended or adjusted under 35 U.S.C. 154(b) by 479 days.

(21) Appl. No.: 11/918,571

(22) PCT Filed: Apr. 26, 2006

(86) PCT No.: PCT/JP2006/308771

§ 371 (c)(1),
(2), (4) Date: Oct. 16, 2007

(87) PCT Pub. No.: WO2006/118159

PCT Pub. Date: Nov. 9, 2006

(65) Prior Publication Data

US 2009/0068283 A1      Mar. 12, 2009

(30) Foreign Application Priority Data

Apr. 28, 2005   (JP)   ............. 2005-133328

(51) Int. Cl.
*A01N 25/00*   (2006.01)
*A01N 59/26*   (2006.01)
*A61K 33/42*   (2006.01)
*A61K 33/38*   (2006.01)

(52) U.S. Cl. .............. 424/405; 424/601; 424/618

(58) Field of Classification Search ............... None
See application file for complete search history.

(56) References Cited

U.S. PATENT DOCUMENTS 5,296,238 A * 3/1994 Sugiura et al. ............. 424/604

FOREIGN PATENT DOCUMENTS

| JP | 60-239313 | 11/1985 |
|---|---|---|
| JP | 3-43457 | 2/1991 |
| JP | 3-83906 | 4/1991 |
| JP | 4-273803 | 9/1992 |
| JP | 5-17112 | 1/1993 |
| JP | 6-48713 | 2/1994 |
| JP | 9-183863 | 7/1997 |

OTHER PUBLICATIONS

C. Jäger, et al.; $^{31}$P and $^{29}$Si NMR Investigations of the Structure of NASICON-Compounds; *Experimentelle Technik der Physik*; vol. 36; No. 4/5; 1988; pp. 339-348 (5 Sheets.).

C. Jäger; "$^{31}$P MAS NMR Study of the NASICON System $Na_{1+4y}Zr_{2-y}(PO_4)_3$;" *Chemical Physics Letter*; vol. 150; No. 6; Sep. 30, 1988; pp. 503-505 (2 sheets).

H. Y-P. Hong; "Crystal Structures and Crystal Chemistry in the System $Na_{1+x}Zr_2Si_xP_{3-x}O_{12}$;" *Mat. Res. Bull.*; vol. 11; 1976; pp. 173-182 (5 Sheets).

* cited by examiner

*Primary Examiner*—Ernst V Arnold
(74) *Attorney, Agent, or Firm*—Kratz, Quintos & Hanson, LLP

(57) ABSTRACT

The present invention is to provide a silver-based inorganic antimicrobial agent that has excellent heat resistance and chemical resistance, that gives little resin coloration, and that has excellent processability.

It has been found that the object can be attained by a silver ion-containing zirconium phosphate represented by Formula (1) below by limiting the production conditions to wet synthesis, and the present invention has thus been accomplished.

$$Ag_aM_bZr_c(PO_4)_3 \cdot nH_2O \qquad (1)$$

In Formula (1), M is at least one type of ion selected from an alkali metal ion, a hydrogen ion, and an ammonium ion, a, b, and c are positive numbers and satisfy $1.5 \leq c \leq 2$ and $a+b+4c=9$, and n is no greater than 2.

15 Claims, No Drawings

SILVER-BASED INORGANIC ANTIMICROBIAL AGENT AND ANTIMICROBIAL PRODUCT

TECHNICAL FIELD

The present invention relates to a silver-supporting zirconium phosphate; this is a novel silver-based inorganic antimicrobial agent that has excellent heat resistance, chemical resistance, and processability and that gives little discoloration when mixed with a plastic. Furthermore, the present invention relates to an antimicrobial product comprising the silver-based inorganic antimicrobial agent.

BACKGROUND ART

In recent years, zirconium phosphate-based inorganic ion exchangers have been utilized in various applications by making use of their characteristics. With regard to the zirconium phosphate-based inorganic ion exchangers, there are amorphous ones, crystalline ones having a 2-dimensional layer structure, and crystalline ones having a 3-dimensional network structure. Among them, hexagonal zirconium phosphate, which has a 3-dimensional network structure, is excellent in terms of heat resistance, chemical resistance, radiation resistance, low thermal expansion properties, etc., and is applied to the immobilization of radioactive waste, solid electrolytes, gas adsorbing/separating agents, catalysts, antimicrobial agent starting materials, etc.

Various hexagonal zirconium phosphates are known to date. Examples thereof include $A_xNH_{4(1-x)}Zr_2(PO_4)_3 \cdot nH_2O$ (ref. e.g. Patent Publication 1), $AZr_2(PO_4)_3 \cdot nH_2O$ (ref. e.g. Patent Publication 2), and $H_nR_{1-n}Zr_2(PO_4)_3 \cdot mH_2O$ (ref. e.g. Patent Publication 3).

Zirconium phosphates in which the ratio of Zr to P varies are also known. Examples thereof include $Na_{1+4x}Zr_{2-x}(PO_4)_3$ (ref. e.g. Nonpatent Publication 1), $Na_{1+2x}Mg_xZr_{2-x}(PO_4)_3$ (ref. e.g. Nonpatent Publications 1 and 2), and $Na_{1+x}Zr_2Si_xP_{3-x}O_{12}$ (ref. e.g. Nonpatent Publications 2 and 3).

With regard to a process for synthesizing these hexagonal zirconium phosphates, a calcination method in which synthesis is carried out by mixing starting materials and then calcining the mixture at 1,000° C. or higher using a calcining furnace, etc., a hydrothermal method in which synthesis is carried out by mixing starting materials in water or in a state in which they contain water and then heating under pressure, a wet method in which synthesis is carried out by mixing starting materials in water and then heating at normal pressure, etc. are known.

Among these methods, the calcination method enables zirconium phosphate having an appropriately adjusted P/Zr ratio to be synthesized just by mixing starting materials and heating them at high temperature. However, in the calcination method it is not easy to mix the starting materials uniformly, and it is difficult to get a zirconium phosphate having a homogeneous composition. Furthermore, since it is necessary to carry out grinding and classification after calcination in order to obtain particles, there are problems with quality and productivity. Moreover, it is obviously impossible to synthesize a crystalline zirconium phosphate containing ammonia by the calcination method. On the other hand, the wet method and the hydrothermal method can give homogeneous fine particulate zirconium phosphate, but apart from one having a P/Zr ratio of 1.5, and one having a P/Zr ratio of 2 represented by Formula (3) below, no crystalline zirconium phosphate is known.

$$NH_4ZrH(PO_4)_2 \quad (3)$$

Silver, copper, zinc, tin, mercury, lead, iron, cobalt, nickel, manganese, arsenic, antimony, bismuth, barium, cadmium, chromium, etc. ions have for a long time been known as metal ions that exhibit antimold properties, antimicrobial properties, and antialgal properties (hereinafter, abbreviated to antimicrobial metal ions). In particular silver ion is widely used as a silver nitrate aqueous solution having a disinfecting action and a sterilizing action. However, many of the above-mentioned metal ions that exhibit antimold properties, antimicrobial properties, or antialgal properties are harmful to the human body; there are various restrictions on the application method, storage method, disposal method, etc., and their applications are also limited.

In order to exhibit antimold properties, antimicrobial properties, and antialgal properties, it is sufficient to apply a trace amount of antimicrobial metal to an application target. Because of this, there have been proposed as antimicrobial agents having antimold properties, antimicrobial properties, and antialgal properties an organic supported antimicrobial agent having an antimicrobial metal ion supported on an ion-exchange resin, a chelate resin, etc. and an inorganic antimicrobial agent having an antimicrobial metal ion supported on a clay mineral, an inorganic ion-exchanger, or a porous body.

With regard to the above-mentioned various types of antimicrobial agents, compared with the organic supported type inorganic antimicrobial agents have the advantages of higher safety, a longer lasting antimicrobial effect and, moreover, excellent heat resistance.

As one of the inorganic antimicrobial agents, an antimicrobial agent in which alkali metal ions such as sodium ions in a clay mineral such as montmorillonite or zeolite are ion-exchanged with silver ions is known. Since the skeleton structure of the clay mineral itself has poor acid resistance, silver ions are easily leached in, for example, an acidic solution, and the antimicrobial effect does not last long.

Furthermore, since silver ions are unstable toward exposure to heat and light and are easily reduced to metallic silver, there are problems with long-term stability, such as coloration being caused.

In order to increase the silver ion stability, there is one in which silver ions and ammonium ions are supported on a zeolite by ion-exchanging so that they coexist. However, the prevention of coloration does not reach a practical level even in this system, and a fundamental solution to the problem has yet to be found.

Furthermore, as another inorganic antimicrobial agent, there is an antimicrobial agent having an antimicrobial metal supported on an adsorptive active carbon. However, in this agent since a soluble antimicrobial metal salt is only physically adsorbed or attached, when contacted with moisture the antimicrobial metal ion is rapidly leached, and the antimicrobial effect does not last long.

Recently, an antimicrobial agent having antimicrobial metal ions supported on a special zirconium phosphate salt has been proposed. For example, one represented by Formula (4) below is known (ref. e.g. Patent Publication 4).

$$M^1M^2_xH_yA_z(PO_4)_2 \cdot nH_2O \quad (4)$$

(In Formula (4), $M^1$ is one type selected from 4-valent metals, $M^2$ is one type selected from silver, copper, zinc, tin, mercury, lead, iron, cobalt, nickel, manganese, arsenic, antimony, bismuth, barium, cadmium, and chromium, A is one type selected from alkali metal ions and alkaline earth metal ions, n is a value satisfying $0 \leq n \leq 6$, and x, y, and z are values satisfying each of $0<(I)\times(x)<2$, $0<y<2.0<z<0.5$, and $(I)\times(x)+y+z=2$, provided that I is the valence of $M^2$.)

This antimicrobial agent is known as a material that is chemically and physically stable and exhibits antimold and antimicrobial properties for a long period of time. However, when it is kneaded with a synthetic resin such as nylon, the entire resin might be colored, the processability is poor due to the particle size, and it cannot be used as a product.

(Patent Publication 1) JP-A-6-48713 (JP-A denotes a Japanese unexamined patent application publication.)

(Patent Publication 2) JP-A-5-17112

(Patent Publication 3) JP-A-60-239313

(Patent Publication 4) JP-A-3-83906

(Nonpatent Publication 1) C. JAGER and three others, '31P and 29Si NMR Investigatios of the Structure of NASICON-Strukturtyps', Expermentelle Technik der Physik, 1988, Vol. 36, No. 4/5, p 339-348

(Nonpatent Publication 2) C. JAGER and two others '31P MAS NMR STUDY OF THE NASICON SYSTEM $Na_{1+y}Zr_{2-y}(PO_4)_3$'. Chemical Physics Letters, 1988, Vol. 150, No. 6, p 503-505

(Nonpatent Publication 3) H. Y-P HONG, 'CRYSTAL STRUCTURE AND CRYSTAL CHEMISTRY IN THE SYSTEM $Na_{1+x}Zr_2Si_xP_{3-x}—O_{12}$', Mat. Res. Bull., Vol. 11, p 173-182

DISCLOSURE OF INVENTION

Problems to be Solved by the Invention

The present invention is to provide a silver-based inorganic antimicrobial agent that has excellent heat resistance and chemical resistance, that gives little resin coloration, and that has excellent processability, and to provide an antimicrobial product employing same.

Means for Solving the Problems

As a result of an intensive investigation by the present inventors in order to solve the above-mentioned problems, it has been found that the problems can be solved by a silver ion-containing zirconium phosphate represented by Formula (1) below, and the present invention has thus been accomplished. The above-mentioned silver ion-containing zirconium phosphate is suitably produced by wet synthesis.

$$Ag_aM_bZr_c(PO_4)_3 \cdot nH_2O \quad (1)$$

In Formula (1), M is at least one type of ion selected from an alkali metal ion, a hydrogen ion, and an ammonium ion, a, b, and c are positive numbers and satisfy $1.5<c<2$ and $a+b+4c=9$, and n is no greater than 2.

Furthermore, the present invention is preferably a silver-based inorganic antimicrobial agent having silver ions supported on a zirconium phosphate represented by Formula (2) below.

$$M_{b1}Zr_c(PO_4)_3 \cdot nH_2O \quad (2)$$

In Formula (2), M is at least one type of ion selected from an alkali metal ion, a hydrogen ion, and an ammonium ion, b1 and c are positive numbers and satisfy $1.5<c<2$ and $b1+4c=9$, and n is no greater than 2.

Furthermore, the present invention is preferably a silver-based inorganic antimicrobial agent employing a zirconium phosphate prepared by a wet synthesis method using greater than 1.5 but less than 2 moles of phosphoric acid or a salt thereof relative to 1 mole of a zirconium compound.

Moreover, the present invention is an antimicrobial product containing the above-mentioned silver-based inorganic antimicrobial agent.

Effects of the Invention

The silver-based inorganic antimicrobial agent of the present invention has excellent antimicrobial activity and discoloration resistance properties compared with existing zirconium phosphate-based antimicrobial agents.

BEST MODE FOR CARRYING OUT THE INVENTION

The present invention is explained below. The silver-based inorganic antimicrobial agent of the present invention is represented by Formula (1) above.

Examples of the alkali metal ion denoted by M in Formula (1) include Li, Na, K, Rb, and Cs, and it may be used on its own or in a combination of a plurality of types. Particularly preferred alkali metal ions are Na ions and K ions from the viewpoint of ion-exchangeability and ease of synthesis, and Na ions are more preferable.

M in Formula (1) is at least one type selected from the group consisting of an alkali metal ion, a hydrogen ion, and an ammonium ion, is preferably one having an alkali metal ion, a hydrogen ion, and an ammonium ion, and is more preferably one having an alkali metal ion and a hydrogen ion.

In Formula (1), a is $0<a$, is preferably at least 0.01, and is more preferably at least 0.03, and in addition a is preferably no greater than 1, and more preferably no greater than 0.6. When a is less than 0.01, sufficient antimicrobial properties might not be exhibited.

In Formula (1), b is $0<b$, is preferably at least 0.1, and is more preferably at least 0.3. It is not preferable for b to be less than 0.1 since discoloration easily occurs in some cases. Furthermore, b is less than 3, preferably less than 2, more preferably no greater than 1.8, yet more preferably no greater than 1.72, and particularly preferably no greater than 1.5.

In Formula (1), b is the total number of alkali metal, hydrogen, and/or ammonium ions. When there is an ammonium ion, there is a case in which no hydrogen ion is present, but when comparing alkali metal ions and hydrogen ions, it is preferable that there are more hydrogen ions.

When there is no ammonium ion, there is a case in which no hydrogen ion is present, but when comparing alkali metal ions and hydrogen ions, it is preferable that there are more hydrogen ions. When there is no ammonium ion, it is preferable for hydrogen ion to be present.

In the present invention, the alkali metal ion is preferably less than 2 in Formula (1), more preferably less than 1.8, and yet more preferably less than 1.4, and it is preferably at least 0.01, more preferably at least 0.03, and yet more preferably at least 0.05.

In the present invention, the hydrogen ion is preferably less than 2 in Formula (1), more preferably less than 1.8, and yet more preferably less than 1.4, and it is preferably at least 0.01, more preferably at least 0.03, and yet more preferably at least 0.05.

In the present invention, the ammonium ion is preferably less than 1 in Formula (1), more preferably less than 0.8, and yet more preferably less than 0.4, and it is preferably at least 0.01, more preferably at least 0.03, and yet more preferably at least 0.05.

In Formula (1), c is $1.5<c<2$, is preferably greater than 1.75, is more preferably at least 1.8, and is yet more preferably at least 1.82. Furthermore, c is preferably less than 1.99, more preferably no greater than 1.98, and yet more preferably no greater than 1.97.

It is not preferable for c to be 1.5 or less since it is difficult to obtain a homogeneous zirconium phosphate represented by Formula (2) in some cases.

In Formula (1), n is no greater than 2, preferably no greater than 1, more preferably 0.01 to 0.5, and yet more preferably 0.03 to 0.3. It is not preferable for n to be greater than 2 since the absolute amount of moisture contained in the silver-based inorganic antimicrobial agent of the present invention is large and foaming or hydrolysis might occur during processing, etc.

As a zirconium phosphate used when synthesizing the silver-based inorganic antimicrobial agent of the present invention, it is preferable to use a zirconium phosphate represented by Formula (2) above.

In Formula (2), M is at least one type of ion selected from the group consisting of an alkali metal ion, a hydrogen ion, and an ammonium ion. b1 and c are positive numbers that satisfy $1.5<c<2$ and $b1+4c=9$, and n is no greater than 2.

A process for synthesizing a zirconium phosphate represented by Formula (2) is a wet method in which various types of starting materials are reacted in an aqueous solution. Specifically, an aqueous solution containing a zirconium compound, ammonia or a salt thereof, oxalic acid or a salt thereof, phosphoric acid or a salt thereof, etc. at predetermined amounts is adjusted so as to have a pH of no greater than 4 and then heated at a temperature of at least 70° C., thus carrying out synthesis. The zirconium phosphate thus synthesized is further filtered, washed well with water, then dried, and lightly ground, thus giving white fine particulate zirconium phosphate.

Examples of a zirconium compound that can be used as a starting material for the synthesis of a zirconium phosphate represented by Formula (2) include zirconium nitrate, zirconium acetate, zirconium sulfate, basic zirconium sulfate, zirconium oxysulfate, and zirconium oxychloride, and zirconium oxychloride is preferable from the viewpoint of reactivity, economy, etc.

Examples of ammonia or a salt thereof that can be used as a starting material for the synthesis of a zirconium phosphate represented by Formula (2) include ammonium chloride, ammonium nitrate, ammonium sulfate, aqueous ammonia, ammonium oxalate, and ammonium phosphate, and ammonium chloride and aqueous ammonia are preferable.

Examples of oxalic acid or a salt thereof that can be used as a starting material for the synthesis of a zirconium phosphate represented by Formula (2) include oxalic acid dihydrate, sodium oxalate, ammonium oxalate, sodium hydrogen oxalate, and ammonium hydrogen oxalate, and oxalic acid dihydrate is preferable.

As phosphoric acid or a salt thereof that can be used as a starting material for the synthesis of a zirconium phosphate represented by Formula (2), a soluble or acid-soluble salt is preferable; examples thereof include phosphoric acid, sodium phosphate, potassium phosphate, and ammonium phosphate, and phosphoric acid is more preferable. The concentration of the phosphoric acid is preferably on the order of 60% to 85%.

The molar ratio of phosphoric acid or a salt thereof to the zirconium compound (the zirconium compound being 1) when synthesizing a zirconium phosphate represented by Formula (2) is greater than 1.5 but less than 2, preferably from 1.51 to less than 1.71, more preferably 1.52 to 1.67, and particularly preferably 1.52 to 1.65.

That is, the process for synthesizing a zirconium phosphate represented by Formula (2) is preferably a wet method in which the number of moles of phosphoric acid or a salt thereof per mole of zirconium compound is greater than 1.5 but less than 2.

Furthermore, the molar ratio of phosphoric acid or a salt thereof to ammonia or a salt thereof (ammonia or a salt thereof being 1) when synthesizing a zirconium phosphate represented by Formula (2) is preferably 0.3 to 10, more preferably 1 to 10, and particularly preferably 2 to 5.

That is, the process for synthesizing a zirconium phosphate represented by Formula (2) is a wet method in which ammonia or a salt thereof is used.

The molar ratio of phosphoric acid or a salt thereof to oxalic acid or a salt thereof (oxalic acid or a salt thereof being 1) when synthesizing a zirconium phosphate represented by Formula (2) is preferably 1 to 6, more preferably 1.5 to 5, yet more preferably 1.51 to 4, and particularly preferably 1.52 to 3.5.

That is, the process for synthesizing a zirconium phosphate represented by Formula (2) is a wet method in which oxalic acid or a salt thereof is used.

The solids concentration of a reaction slurry when synthesizing a zirconium phosphate represented by Formula (2) is preferably at least 3 wt %, and more preferably from 7% to 15 wt % from the viewpoint of economic etc. efficiency.

The pH when synthesizing a zirconium phosphate represented by Formula (2) is preferably at least 1 but no greater than 4, more preferably 1.5 to 3.5, yet more preferably 2 to 3, and particularly preferably 2.2 to 3. It is not preferable for the pH to be greater than 4 since a zirconium phosphate represented by Formula (2) cannot be synthesized in some cases. It is not preferable for the pH to be less than 1 since a zirconium phosphate represented by Formula (2) cannot be synthesized in some cases. For adjustment of the pH, it is preferable to use sodium hydroxide, potassium hydroxide, aqueous ammonia, etc., and it is more preferable to use sodium hydroxide.

The synthesis temperature when synthesizing a zirconium phosphate represented by Formula (2) is preferably at least 70° C., more preferably at least 80° C., yet more preferably at least 90° C., and particularly preferably at least 95° C. Furthermore, the synthesis temperature is preferably no higher than 150° C., and more preferably no higher than 120° C. It is not preferable for the temperature to be less than 70° C. since the zirconium phosphate of the present invention cannot be synthesized in some cases. It is not preferable for the temperature to be higher than 150° C. since it is disadvantageous in terms of energy.

It is desirable to carry out stirring when synthesizing a zirconium phosphate represented by Formula (2) so that the starting materials are homogenously mixed and the reaction proceeds uniformly.

The time for synthesis of a zirconium phosphate represented by Formula (2) depends on the synthesis temperature. For example, the time for synthesis of the zirconium phosphate of the present invention is preferably at least 4 hours, more preferably 8 to 72 hours, and yet more preferably 10 to 48 hours.

As a zirconium phosphate represented by Formula (2), it is possible to synthesize one having a median diameter of 0.1 to 5 μm. The median diameter of a zirconium phosphate represented by Formula (2) is preferably 0.1 to 5 μm, more preferably 0.2 to 3 μm, and yet more preferably 0.3 to 2 μm. When the processability into various types of products is taken into consideration, not only the median diameter but also the maximum particle diameter and the spread are important. From this point, the maximum particle diameter of a zirconium phosphate represented by Formula (2) is preferably no greater than 10 μm, and more preferably no greater than 8 μm, and it is particularly preferable for it to be no greater than 6 μm since an effect can be exhibited. The standard deviation for the median diameter is preferably no greater than 1, and it is more preferable for it to be no greater than 0.5 since an effect can be exhibited more effectively.

Furthermore, a silver-based inorganic antimicrobial agent represented by Formula (1), which is obtained by subjecting a zirconium phosphate represented by Formula (2) to silver ion exchange, preferably has the same median diameter, maximum particle diameter, and standard deviation as those of the zirconium phosphate of Formula (2) above. Since there is hardly any change in the median diameter, the maximum particle diameter, and the standard deviation as a result of silver ion exchange, by setting the median diameter, the maximum particle diameter, and the standard deviation of the zirconium phosphate represented by Formula (2) so as to be in the above-mentioned ranges it is possible to set the median diameter, the maximum particle diameter, and the standard deviation of the silver-based inorganic antimicrobial agent represented by Formula (1) in desired ranges.

As examples of zirconium phosphates represented by Formula (2), which can be used as starting materials for the silver-based inorganic antimicrobial agent of the present invention, those listed below can be cited. However, since those having ammonium ion have low ion-exchangeability, when a high silver ion exchange rate is required, the ammonium ion may be eliminated by carrying out calcination, etc. as necessary, thus giving an H type, which has high ion-exchangeability.

$(NH_4)_{1.4}Zr_{1.9}(PO_4)_3 \cdot 0.05H_2O$ $(NH_4)_{1.24}Zr_{1.94}(PO_4)_3 \cdot 0.15H_2O$ $Na_{0.6}(NH_4)_{0.84}Zr_{1.89}(PO_4)_3 \cdot 0.3H_2O$ $Na(NH_4)_{0.44}Zr_{1.89}(PO_4)_3 \cdot 0.2H_2O$ $Na_{0.6}H_{0.3}(NH_4)_{0.42}Zr_{1.92}(PO_4)_3 \cdot 0.2H_2O$ $K_{0.92}(NH_4)_{0.44}Zr_{1.91}(PO_4)_3 \cdot 0.1H_2O$ $Na_{0.72}(NH_4)Zr_{1.82}(PO_4)_3 \cdot 0.2H_2O$ $Na_{0.3}H_{0.34}(NH_4)Zr_{1.84}(PO_4)_3 \cdot 0.1H_2O$ $Na(NH_4)_{0.76}Zr_{1.81}(PO_4)_3 \cdot 0.1H_2O$ $Na_{0.6}H_{0.4}(NH_4)_{0.6}Zr_{1.85}(PO_4)_3 \cdot 0.3H_2O$ $Na_{1.2}Zr_{1.95}(PO_4)_3 \cdot 0.1H_2O$ $Na_{0.24}H_{1.36}Zr_{1.85}(PO_4)_3 \cdot 0.11H_2O$ $H_{1.4}Zr_{1.9}(PO_4)_3 \cdot 0.15H_2O$ $K_{0.6}H_{0.6}Zr_{1.95}(PO_4)_3 \cdot 0.1H_2O$ $Na_{1.12}Zr_{1.97}(PO_4)_3$ $NaH_{0.12}Zr_{1.97}(PO_4)_3$ $Na_{0.48}Zr_{1.88}(PO_4)_3$ $Na_{0.48}HZr_{1.88}(PO_4)_3$ $Na_{0.72}HZr_{1.82}(PO_4)_3$ $Na_{0.6}H_{1.12}Zr_{1.82}(PO_4)_3$ In order to obtain the silver-based inorganic antimicrobial agent of the present invention, it is necessary to subject a zirconium phosphate represented by Formula (2) to silver ion exchange. A method for carrying out this silver ion exchange may involve immersing a zirconium phosphate represented by Formula (2) in an aqueous solution containing an appropriate concentration of silver ion. It is preferable to carry out stirring, etc. during this immersion, thus making a uniformly mixed state. The amount immersed may be a concentration that can be mixed with the aqueous solution uniformly, and the zirconium phosphate represented by Formula (2) is preferably no greater than 20 wt %. For the preparation of an aqueous solution containing silver ions, it is preferable to use an aqueous solution in which silver nitrate is dissolved in ion-exchanged water. The temperature of the aqueous solution at the time of ion exchange may be 0° C. to 100° C. and is preferably 20° C. to 80° C. Since this ion exchange takes place quickly, the immersion time may be less than 5 min, but in order to obtain a uniform and high silver ion exchange rate, it is preferably 30 min to 5 hours. Even if this is carried out for 5 hours or more, there are cases in which silver ion exchange does not progress further.

After completion of the silver ion exchange, this is washed well with ion-exchanged water etc. and dried, thus giving the silver-based inorganic antimicrobial agent of the present invention.

In order to improve the discoloration resistance of the silver-based inorganic antimicrobial agent of the present invention, it is preferable to calcine the silver-based inorganic antimicrobial agent obtained above. This calcination for improving the discoloration resistance may be carried out prior to silver ion exchange, but in order to obtain sufficient discoloration resistance, it is particularly preferable to carry it out subsequent to silver ion exchange. The calcination temperature is preferably 550° C. to 1,000° C., more preferably 600° C. to 900° C., and yet more preferably 650° C. to 800° C. in order to improve the discoloration resistance. The calcination time is preferably at least 1 hour, more preferably at least 2 hours, and yet more preferably at least 4 hours in order to improve the discoloration resistance. This calcination time is preferably no longer than 48 hours, and more preferably no longer than 36 hours.

After completion of the calcination, if left as it is for a long period of time, there is a possibility of moisture absorption, and it is therefore preferable to cool within 24 hours, and more preferably within 18 hours. Since the silver-based inorganic antimicrobial agent of the present invention sometimes aggregates after calcination, the aggregated material may be ground using a grinder. In this case, taking into consideration moisture absorption, etc., the grinding time is better to be short.

Examples of the silver-based inorganic antimicrobial agent of the present invention are as follows.

$Ag_{0.2}H_{1.2}Zr_{1.9}(PO_4)_3 \cdot 0.05H_2O$ $Ag_{0.1}H_{1.14}Zr_{1.94}(PO_4)_3 \cdot 0.15H_2O$ $Ag_{0.2}Na_{0.4}(NH_4)_{0.84}Zr_{1.89}(PO_4)_3 \cdot 0.3H_2O$ $Ag_{0.3}Na_{0.1}H_{1.04}Zr_{1.89}(PO_4)_3 \cdot 0.2H_2O$ $Ag_{0.5}Na_{0.2}H_{0.3}(NH_4)_{0.32}Zr_{1.92}(PO_4)_3 \cdot 0.2H_2O$ $Ag_{0.4}K_{0.6}H_{0.36}Zr_{1.91}(PO_4)_3 \cdot 0.1H_2O$ The form of the silver-based inorganic antimicrobial agent of the present invention when used is not particularly limited, and it may be mixed with another component as appropriate according to the intended purpose or made into a composite with another material. For example, the silver-based inorganic antimicrobial agent of the present invention may be used in various forms such as a powder, a powder-containing dispersion, powder-containing particles, a powder-containing paint, a powder-containing fiber, a powder-containing paper, a powder-containing plastic, a powder-containing film, or a powder-containing aerosol and, moreover, various types of additives or materials such as a deodorant, a flame retardant, a corrosion inhibitor, a fertilizer, or a building material may be used in combination as necessary.

The silver-based inorganic antimicrobial agent of the present invention may contain various types of additives as necessary in order to improve the ease of kneading into a resin or other physical properties. Specific examples thereof include a pigment such as zinc oxide or titanium oxide, an inorganic ion-exchanger such as zirconium phosphate or a zeolite, a dye, an antioxidant, a light stabilizer, a flame retardant, an antistatic agent, a foaming agent, an impact modifier, glass fiber, a lubricant such as a metal soap, a desiccant, a filler, a coupling agent, a nucleating agent, a flowability improving agent, a deodorant, wood flour, a fungicide, an antifoulant, a corrosion inhibitor, a metal powder, a UV absorber, and a UV shielding agent.

An antimicrobial resin composition can easily be obtained by adding the silver-based inorganic antimicrobial agent of the present invention to a resin. The type of resin that can be used is not particularly limited; the resin may be any of a natural resin, a synthetic resin, and a semi-synthetic resin, and the resin may be either a thermoplastic resin or a thermosetting resin. The resin may be any one of a resin for molding, a resin for fiber, and a rubber resin, and specific examples of the resin include resins for molding or fiber such as polyethylene, polypropylene, vinyl chloride, ABS resin, AS resin, MBS resin, nylon resin, polyester, polyvinylidene chloride, polystyrene, polyacetal, polycarbonate, PBT, acrylic resin, fluorine resin, polyurethane elastomer, polyester elastomer, melamine, urea resin, ethylene tetrafluoride resin, unsaturated polyester resin, rayon, acetate, acrylic, polyvinyl alcohol, cupra, triacetate, and vinylidene, and rubber resins such as natural rubber, silicone rubber, styrene butadiene rubber, ethylene propylene rubber, fluorine rubber, nitrile rubber, chlorosulfonated polyethylene rubber, butadiene rubber, synthetic natural rubber, butyl rubber, urethane rubber, and acrylic rubber. The silver-based inorganic antimicrobial agent of the present invention may be formed into a composite with a fiber such as a natural fiber, thus giving an antimicrobial fiber.

The proportion of the silver-based inorganic antimicrobial agent of the present invention in the antimicrobial resin composition is preferably 0.03 to 5 parts by weight relative to 100 parts by weight of the antimicrobial resin composition, and more preferably 0.1 to 2.0 parts by weight. If it is less than 0.03 parts by weight, the antimicrobial properties of the antimicrobial resin composition might be insufficient, and on the other hand if it is present at more than 5 parts by weight, there is hardly any further improvement of the antimicrobial effect, it is not cost-effective, and the physical properties of the resin might be greatly degraded.

A method for adding the silver-based inorganic antimicrobial agent of the present invention to a resin and processing into a resin molding may be any known method. For example, there are (1) a method in which an attachment agent for enhancing the adhesion between a silver-based inorganic antimicrobial agent powder and a resin or a dispersant for improving the dispersibility of the antimicrobial agent powder is used, and mixing with the resin in the form of pellets or a powder is carried out directly in a mixer, (2) a method in which mixing is carried out as described above, the mixture is molded into pellets using an extruder, and this molding is then added to resin pellets, (3) a method in which the silver-based inorganic antimicrobial agent is molded into high concentration pellets using a wax, and the pellets thus molded are then added to resin pellets, and (4) a method in which a paste composition is prepared by mixing and dispersing the silver-based inorganic antimicrobial agent in a highly viscous liquid such as a polyol, and this paste is then added to resin pellets.

When molding the above-mentioned antimicrobial resin composition, any known processing techniques and equipment may be used, according to the characteristics of various types of resins. Preparation can be easily carried out by a mixing, addition, or kneading method while heating at an appropriate temperature and applying an appropriate increased or decreased pressure; specific operations may be carried out by a standard method, and moldings in various forms such as lump, sponge, film, sheet, filament, pipe, or a composite thereof may be obtained.

The form in which the silver-based inorganic antimicrobial agent of the present invention is used is not particularly limited, and it is not limited to being added to a resin molding or a polymer compound. It may be mixed, according to the intended purpose where antimold, antialgal, and antimicrobial properties are required, with another component as appropriate or may be made into a composite with another material. For example, it may be used in various forms such as a powder, a powder-containing dispersion, granules, an aerosol, or a liquid.

Application

The silver-based inorganic antimicrobial agent of the present invention can be used in various fields where antimold, antialgal, and antimicrobial properties are required, that is, it can be used as an electrical appliance, a kitchen product, a fiber product, a housing/building material product, a toiletry product, a paper product, a toy, a leather product, stationery, and other products.

To illustrate more specific applications, examples of the electrical appliances include dish washers, dish dryers, refrigerators, washing machines, kettles, televisions, personal computers, radio cassettes, cameras, video cameras, water purifiers, rice cookers, vegetable cutters, cash registers, bedding dryers, faxes, ventilators, and air-conditioners, and examples of the kitchen products include tableware, chopping boards, straw cutters, trays, chopsticks, teapots, thermos flasks, knives, ladle handles, turners, lunch boxes, rice spoons, bowls, colanders, sink strainers, scouring brush containers, bins, and draining bags.

Examples of the fiber products include shower curtains, cotton batting, air-conditioner filters, stockings, socks, napkins, sheets, bedding covers, pillows, gloves, aprons, curtains, diapers, bandages, masks, and sportswear, and examples of the housing/building materials include decorative boards, wall paper, flooring boards, window films, handles, carpets, mats, artificial marble, handrails, jointing, tiles, and waxes. Examples of the toiletry products include toilet seats, bathtubs, tiles, chamber pots, bins, toilet brushes, bathtub covers, pumice stones, soap containers, bathroom chairs, clothes baskets, showers, and washbasins, examples of the paper products include wrapping paper, powder paper, medicine boxes, sketch books, medical charts, exercise books, and origami paper, and examples of the toys include dolls, soft toys, papier-mache, blocks, and puzzles.

Examples of the leather products include shoes, bags, belts, watch straps, interior products, chairs, gloves, and hanging straps, and examples of the stationery include ball-point pens, mechanical pencils, pencils, erasers, crayons, paper, notebooks, floppy disks, rulers, Post-it, and staplers. Examples of the other products include insoles, cosmetics containers, scouring brushes, powder puffs, hearing aids, musical instruments, cigarette filters, adhesive paper sheets for cleaning, hanging strap handles, sponges, kitchen towels, cards, microphones, hairdressing articles, vending machines, razors, telephones, medical thermometers, stethoscopes, slippers, clothing cases, toothbrushes, sandpit sand, food wrapping films, antimicrobial sprays, and paint.

EXAMPLES

The present invention is explained below by reference to Examples, but the present invention should not be construed as being limited thereby.

The median diameter was measured using laser diffraction type particle size distribution on a volume basis, and the standard deviation was determined from the measurement results.

The amount of zirconium was calculated by first dissolving a sample using a strong acid and subjecting this liquid to measurement with an ICP emission spectrophotometer. The amount of phosphorus was calculated by first dissolving a sample using a strong acid and subjecting this liquid to measurement with an ICP emission spectrophotometer. The amounts of sodium and potassium were calculated by first dissolving a sample using a strong acid and subjecting this liquid to measurement with an atomic absorption spectrometer. The amount of ammonia was calculated by first dissolving a sample using a strong acid and subjecting this liquid to measurement by an indophenol method.

Synthetic Example 1

After 0.1 mol of oxalic acid dihydrate, 0.195 mol of zirconium oxychloride octahydrate, and 0.1 mol of ammonium chloride were dissolved in 300 mL of pure water, 0.3 mol of phosphoric acid was added thereto while stirring. The pH of this solution was adjusted to 2.7 using a 20% aqueous solution of sodium hydroxide, and the solution was then stirred at 98° C. for 14 hours. Subsequently, the precipitate thus obtained was washed well and dried at 120° C., thus synthesizing a zirconium phosphate compound.

When the compositional formula etc. of this zirconium phosphate compound was measured, the compositional formula was $Na_{0.5}(NH_4)_{0.67}Zr_{1.95}(PO_4)_3 \cdot 0.11H_2O$.

Synthetic Example 2

After 0.1 mol of oxalic acid dihydrate, 0.19 mol of zirconium oxychloride octahydrate, and 0.1 mol of ammonium chloride were dissolved in 300 mL of pure water, 0.3 mol of phosphoric acid was added thereto while stirring. The pH of this solution was adjusted to 2.7 using a 20% aqueous solution of sodium hydroxide, and the solution was then stirred at 98° C. for 14 hours. Subsequently, the precipitate thus obtained was washed well and dried at 120° C., thus synthesizing a zirconium phosphate compound.

When the compositional formula etc. of this zirconium phosphate compound was measured, the compositional formula was $Na_{0.235}(NH_4)_{1.36}Zr_{1.85}(PO_4)_3 \cdot 0.13H_2O$.

Synthetic Example 3

After 0.1 mol of oxalic acid dihydrate, 0.19 mol of zirconium oxychloride octahydrate, and 0.15 mol of ammonium chloride were dissolved in 300 mL of pure water, 0.3 mol of phosphoric acid was added thereto while stirring. The pH of this solution was adjusted to 2.7 using a 20% aqueous solution of sodium hydroxide, and the solution was then stirred at 98° C. for 14 hours. Subsequently, the precipitate thus obtained was washed well and dried at 120° C., thus synthesizing a zirconium phosphate compound.

When the compositional formula etc. of this zirconium phosphate compound was measured, the compositional formula was $Na_{0.54}(NH_4)_{0.86}Zr_{1.9}(PO_4)_3 \cdot 0.12H_2O$.

Synthetic Example 4

After 0.1 mol of oxalic acid dihydrate, 0.195 mol of zirconium oxychloride octahydrate, and 0.11 mol of ammonium chloride were dissolved in 300 mL of pure water, 0.3 mol of phosphoric acid was added thereto while stirring. The pH of this solution was adjusted to 2.9 using a 20% aqueous solution of sodium hydroxide, and the solution was then stirred at 98° C. for 14 hours. Subsequently, the precipitate thus obtained was washed well and dried at 120° C., thus synthesizing a zirconium phosphate.

When the compositional formula etc. of this zirconium phosphate was measured, the compositional formula was $Na_{0.5}(NH_4)_{0.7}Zr_{1.95}(PO_4)_3 \cdot 0.1H_2O$, and the median diameter was 0.45 μm.

Synthetic Example 5

After 0.1 mol of oxalic acid dihydrate, 0.185 mol of zirconium oxychloride octahydrate, and 0.14 mol of ammonium chloride were dissolved in 300 mL of pure water, 0.3 mol of phosphoric acid was added thereto while stirring. The pH of this solution was adjusted to 2.9 using a 20% aqueous solution of sodium hydroxide, and the solution was then stirred at 98° C. for 14 hours. Subsequently, the precipitate thus obtained was washed well and dried at 120° C., thus synthesizing a zirconium phosphate.

When the compositional formula etc. of this zirconium phosphate was measured, the compositional formula was $Na_{0.24}(NH_4)_{1.36}Zr_{1.85}(PO_4)_3 \cdot 0.11H_2O$, and the median diameter was 0.42 μm.

Synthetic Example 6

After 0.1 mol of oxalic acid dihydrate and 0.19 mol of zirconium oxychloride octahydrate were dissolved in 300 mL of pure water, 0.3 mol of phosphoric acid was added thereto while stirring. The pH of this solution was adjusted to 2.9 using 28% aqueous ammonia, and the solution was then stirred at 98° C. for 14 hours. Subsequently, the precipitate thus obtained was washed well and dried at 120° C., thus synthesizing a zirconium phosphate.

When the compositional formula etc. of this zirconium phosphate was measured, the compositional formula was $(NH_4)_{1.4}Zr_{1.9}(PO_4)_3 \cdot 0.15H_2O$, and the median diameter was 0.30 μm.

Synthetic Example 7

After 0.1 mol of oxalic acid dihydrate, 0.195 mol of zirconium oxychloride octahydrate, and 0.07 mol of ammonium chloride were dissolved in 300 mL of pure water, 0.3 mol of phosphoric acid was added thereto while stirring. The pH of this solution was adjusted to 2.7 using a 20% aqueous solution of sodium hydroxide, and the solution was then stirred at 98° C. for 14 hours. Subsequently, the precipitate thus obtained was washed well and dried at 120° C., thus synthesizing a zirconium phosphate.

When the compositional formula etc. of this zirconium phosphate was measured, the compositional formula was $Na_{0.8}(NH_4)_{0.4}Zr_{1.95}(PO_4)_3 \cdot 0.09H_2O$, and the median diameter was 0.45 μm.

Synthetic Example 8

After 0.1 mol of oxalic acid dihydrate and 0.195 mol of zirconium oxychloride octahydrate were dissolved in 300 mL of pure water, 0.3 mol of phosphoric acid was added thereto while stirring. The pH of this solution was adjusted to 2.7 using a 20% aqueous solution of sodium hydroxide, and the solution was then stirred at 98° C. for 14 hours. Subsequently, the precipitate thus obtained was washed well and dried at 120° C., thus synthesizing a zirconium phosphate.

When the compositional formula etc. of this zirconium phosphate was measured, the compositional formula was $Na_{1.2}Zr_{1.95}(PO_4)_3 \cdot 0.1H_2O$, and the median diameter was 0.44 μm.

Synthetic Example 9

After 0.1 mol of oxalic acid dihydrate, 0.185 mol of zirconium oxychloride octahydrate, and 0.14 mol of ammonium chloride were dissolved in 300 mL of pure water, 0.3 mol of phosphoric acid was added thereto while stirring. The pH of this solution was adjusted to 2.9 using a 20% aqueous solution of sodium hydroxide, and the solution was then stirred at 98° C. for 14 hours. Subsequently, the precipitate thus obtained was washed well, dried at 120° C., and further calcined at 700° C. for 4 hours, thus synthesizing a zirconium phosphate.

When the compositional formula etc. of this zirconium phosphate was measured, the compositional formula was $Na_{0.24}H_{1.36}Zr_{1.85}(PO_4)_3 \cdot 0.11H_2O$, and the median diameter was 0.43 μm.

Synthetic Example 10

After 0.1 mol of oxalic acid dihydrate and 0.19 mol of zirconium oxychloride octahydrate were dissolved in 300 mL of pure water, 0.3 mol of phosphoric acid was added thereto while stirring. The pH of this solution was adjusted to 2.9 using 28% aqueous ammonia, and the solution was then stirred at 98° C. for 14 hours. Subsequently, the precipitate thus obtained was washed well, dried at 120° C., and further calcined at 700° C. for 4 hours, thus synthesizing a zirconium phosphate.

When the compositional formula etc. of this zirconium phosphate was measured, the compositional formula was $H_{1.4}Zr_{1.9}(PO_4)_3 \cdot 0.15H_2O$, and the median diameter was 0.30 μm.

Synthetic Example 11

After 0.1 mol of oxalic acid dihydrate, 0.195 mol of zirconium oxychloride octahydrate, and 0.07 mol of ammonium chloride were dissolved in 300 mL of pure water, 0.3 mol of phosphoric acid was added thereto while stirring.

The pH of this solution was adjusted to 2.7 using a 20% aqueous solution of potassium hydroxide, and the solution was then stirred at 98° C. for 14 hours. Subsequently, the precipitate thus obtained was washed well, dried at 120° C., and further calcined at 700° C. for 4 hours, thus synthesizing a zirconium phosphate.

When the compositional formula etc. of this zirconium phosphate was measured, the compositional formula was $K_{0.6}H_{0.6}Zr_{1.95}(PO_4)_3 \cdot 0.1H_2O$, and the median diameter was 0.45 μm.

Example 1

0.09 mol of the zirconium phosphate synthesized in Synthetic Example 1 was added to 450 mL of a 1 N aqueous solution of nitric acid in which 0.004 mol of silver nitrate had been dissolved, and the mixture was stirred at 60° C. for 2 hours so as to support silver. Subsequently, it was washed well, dried at 120° C., and then calcined at 720° C. for 4 hours. The powder after calcining was lightly ground, thereby giving a silver-based inorganic antimicrobial agent of the present invention. When the compositional formula of this silver-based inorganic antimicrobial substance was measured, the compositional formula was $Ag_{0.07}Na_{0.48}H_{0.67}Zr_{1.95}(PO_4)_3 \cdot 0.1H_2O$.

The median diameter (μm) of this silver-based inorganic antimicrobial substance, the standard deviation of the median diameter, the maximum particle diameter (μm), and the minimum inhibitory concentration (MIC, μg/mL) for *E. coli* were measured, and the results are given in Table 1.

Example 2

0.09 mol of the zirconium phosphate synthesized in Synthetic Example 2 was added to 450 mL of a 1 N aqueous solution of nitric acid in which 0.015 mol of silver nitrate had been dissolved, and the mixture was stirred at 60° C. for 2 hours so as to support silver. Subsequently, it was washed well, dried at 120° C., and then calcined at 720° C. for 4 hours. The powder after calcining was lightly ground, thereby giving a silver-based inorganic antimicrobial agent of the present invention. When the compositional formula of this silver-based inorganic antimicrobial substance was measured, the compositional formula was $Ag_{0.17}Na_{0.07}H_{1.36}Zr_{1.85}(PO_4)_3 \cdot 0.11H_2O$.

The median diameter (μm) of this silver-based inorganic antimicrobial substance, the standard deviation of the median diameter, the maximum particle diameter (μm), and the minimum inhibitory concentration (MIC, μg/mL) for *E. coli* were measured, and the results are given in Table 1.

Example 3

0.09 mol of the zirconium phosphate synthesized in Synthetic Example 3 was added to 450 mL of a 1 N aqueous solution of nitric acid in which 0.045 mol of silver nitrate had been dissolved, and the mixture was stirred at 60° C. for 2 hours so as to support silver. Subsequently, it was washed well, dried at 120° C., and then calcined at 720° C. for 4 hours. The powder after calcining was lightly ground, thereby giving a silver-based inorganic antimicrobial agent of the present invention. When the compositional formula of this silver-based inorganic antimicrobial substance was measured, the compositional formula was $$Ag_{0.44}Na_{0.1}H_{0.86}Zr_{1.9}(PO_4)_3 \cdot 0.12H_2O.$$

The median diameter (μm) of this silver-based inorganic antimicrobial substance, the standard deviation of the median diameter, the maximum particle diameter (μm), and the minimum inhibitory concentration (MIC, μg/mL) for *E. coli* were measured, and the results are given in Table 1.

Comparative Example 1

After 0.1 mol of oxalic acid dihydrate, 0.2 mol of zirconium oxychloride octahydrate, and 0.05 mol of ammonium chloride were dissolved in 300 mL of pure water, 0.3 mol of phosphoric acid was added thereto while stirring. The pH of this solution was adjusted to 3.5 using a 20% aqueous solution of sodium hydroxide, and the solution was then stirred at 98° C. for 14 hours. Subsequently, the precipitate thus obtained was washed well and then dried at 120° C., thus synthesizing a zirconium phosphate.

0.09 mol of the zirconium phosphate synthesized above was added to 450 mL of a 1 N aqueous solution of nitric acid in which 0.004 mol of silver nitrate had been dissolved, and the mixture was stirred at 60° C. for 2 hours so as to support silver. Subsequently, the precipitate thus obtained was washed well and dried at 120° C., and the powder after drying then lightly ground, thereby giving a comparative silver-based inorganic antimicrobial agent. When the compositional formula of this comparative silver-based inorganic antimicrobial substance was measured, the compositional formula was $$Ag_{0.07}Na_{0.45}(NH_4)_{0.48}Zr_2(PO_4)_3 \cdot 0.11H_2O.$$

The median diameter (μm) of this comparative silver-based inorganic antimicrobial substance, the standard deviation of the median diameter, the maximum particle diameter (μm), and the minimum inhibitory concentration (MIC, μg/mL) for *E. coli* were measured, and the results are given in Table 1.

Comparative Example 2

After 0.1 mol of oxalic acid dihydrate and 0.2 mol of zirconium oxychloride octahydrate were dissolved in 300 mL of pure water, 0.3 mol of phosphoric acid was added thereto while stirring. The pH of this solution was adjusted to 3.6 using a 20% aqueous solution of sodium hydroxide, and the solution was then stirred at 98° C. for 14 hours. Subsequently, the precipitate thus obtained was washed well and dried at 120° C., thus synthesizing a zirconium phosphate.

0.09 mol of the zirconium phosphate synthesized above was added to 450 mL of a 1 N aqueous solution of nitric acid in which 0.015 mol of silver nitrate had been dissolved, and the mixture was stirred at 60° C. for 2 hours so as to support silver. Subsequently, the precipitate thus obtained was washed well, dried at 120° C., and then calcined at 770° C. for 4 hours. The powder after calcining was lightly ground, thereby giving a comparative silver-based inorganic antimicrobial agent. When the compositional formula of this comparative silver-based inorganic antimicrobial substance was measured, the compositional formula was $$Ag_{0.07}Na_{0.45}(NH_4)_{0.48}Zr_2(PO_4)_3 \cdot 0.11H_2O.$$

The median diameter (μm) of this comparative silver-based inorganic antimicrobial substance, the standard deviation of the median diameter, the maximum particle diameter (μm), and the minimum inhibitory concentration (MIC, μg/mL) for *E. coli* were measured, and the results are given in Table 1.

Comparative Example 3

After 0.1 mol of oxalic acid dihydrate, 0.2 mol of zirconium oxychloride octahydrate, and 0.05 mol of ammonium chloride were dissolved in 300 mL of pure water, 0.3 mol of phosphoric acid was added thereto while stirring. The pH of this solution was adjusted to 3.6 using a 20% aqueous solution of sodium hydroxide, and the solution was then stirred at 98° C. for 14 hours. Subsequently, the precipitate thus obtained was washed well and dried at 120° C., thus synthesizing a zirconium phosphate.

0.09 mol of the zirconium phosphate synthesized above was added to 450 mL of a 1 N aqueous solution of nitric acid in which 0.045 mol of silver nitrate had been dissolved, and the mixture was stirred at 60° C. for 2 hours so as to support silver. Subsequently, the precipitate thus obtained was washed well, dried at 120° C., and then calcined at 770° C. for 4 hours. The powder after calcining was lightly ground, thereby giving a comparative silver-based inorganic antimicrobial agent. When the compositional formula of this comparative silver-based inorganic antimicrobial substance was measured, the compositional formula was $$Ag_{0.44}Na_{0.22}H_{0.34}Zr_2(PO_4)_3 \cdot 0.11H_2O.$$

The median diameter (μm) of this comparative silver-based inorganic antimicrobial substance, the standard deviation of the median diameter, the maximum particle diameter (μm), and the minimum inhibitory concentration (MIC, μg/mL) for *E. coli* were measured, and the results are given in Table 1.

TABLE 1

|  | Median diameter (μm) | Standard deviation | Maximum particle diameter (μm) | MIC (μg/mL) |
| --- | --- | --- | --- | --- |
| Ex. 1 | 0.39 | 0.24 | 1.3 | 62.5 |
| Ex. 2 | 0.42 | 0.20 | 1.4 | 62.5 |
| Ex. 3 | 0.40 | 0.19 | 1.4 | 31.25 |
| Comp. Ex. 1 | 0.56 | 0.32 | 2.3 | 250 |
| Comp. Ex. 2 | 0.60 | 0.57 | 3.1 | 125 |
| Comp. Ex. 3 | 1.3 | 0.78 | 3.3 | 62.5 |

Example 4

Evaluation of Molding

The silver-based inorganic antimicrobial agent obtained in Example 1 was added at 0.15% to a Nylon 6 resin manufactured by Ube Industries, Ltd., and the mixture was subjected to injection molding at 280° C. to give a 2 mm thick plate, thus giving a molding a. The L/a/b color values of this molding a and its color difference ΔE from that of a plate to which no antimicrobial agent had been added were measured using a colorimeter. The results are given in Table 2. Furthermore, an antimicrobial property test was carried out using this injection-molded plate by a test method in accordance with JIS Z28015.2, Plastic Products, etc. The antimicrobial activity value thus obtained is also given in Table 2.

Similarly, moldings b and c and comparative moldings d to f were prepared using the silver-based inorganic antimicrobial agents of Examples 2 and 3 and the comparative silver-based inorganic antimicrobial agents of Comparative Examples 1 to 3. The color values and the antimicrobial activity of these moldings were also measured, and the results are given in Table 2.

TABLE 2

|  | Color values L/a/b | Color difference ΔE | Antimicrobial activity | |
|---|---|---|---|---|
|  |  |  | Staphylococcus aureus | E. Coli |
| Molding a (Ex. 1) | 61.4/−0.7/−1.9 | 5.4 | 4.5< | 5.2< |
| Molding b (Ex. 2) | 63.4/−0.5/−0.9 | 4.3 | 4.5< | 5.2< |
| Molding c (Ex. 3) | 60.4/−1.6/2.4 | 3.9 | 4.5< | 5.2< |
| Comp. Molding d (Comp. Ex. 1) | 43.4/−3.5/29.8 | 38 | 4.2 | 5.2< |
| Comp. Molding e (Comp. Ex. 2) | 57.8/−2.5/21.9 | 25 | 4.0 | 5.0 |
| Comp. Molding f (Comp. Ex. 3) | 54.2/−2.0/11.7 | 17.3 | 4.1 | 4.8 |

Example 5

Polyester Spinning Test

The silver-based inorganic antimicrobial agent prepared in Example 1 was added at 10 wt % to a polyester resin (MA2103, manufactured by Unitika Ltd.) to give a master batch. This master batch was then mixed with polyester resin pellets to give an antimicrobial resin containing 1 wt % of the silver-based inorganic antimicrobial agent. The antimicrobial resin was subjected to melt spinning using a multifilament spinning machine at a spinning temperature of 275° C. and a windup speed of 4000 m/minute, and a 24 filament antimicrobial agent-containing polyester fiber was wound up in drum form to give an antimicrobial agent-containing polyester fiber (antimicrobial fiber a). Filament formation properties were evaluated with respect to filter pressure increase, filament breakage, and the state of wear of a ceramic guide made of alumina during this process. The results are given in Table 3.

Similarly, an antimicrobial agent-containing polyester fiber (antimicrobial fiber b) was obtained using the silver-based inorganic antimicrobial agent prepared in Example 2. Furthermore, an antimicrobial agent-containing polyester fiber (antimicrobial fiber c) was obtained using the silver-based inorganic antimicrobial agent prepared in Example 3. Moreover, a comparative antimicrobial agent-containing polyester fiber (comparative antimicrobial fiber d) was obtained in the same manner as for antimicrobial fiber a using the comparative silver-based inorganic antimicrobial agent prepared in Comparative Example 1. Similarly, a comparative antimicrobial agent-containing polyester fiber (comparative antimicrobial fiber e) was obtained using the comparative silver-based inorganic antimicrobial agent prepared in Comparative Example 2, and a comparative antimicrobial agent-containing polyester fiber (comparative antimicrobial fiber f) was obtained using the comparative silver-based inorganic antimicrobial agent prepared in Comparative Example 3.

The target polyester fiber was also prepared in the same manner but without using a silver-based inorganic antimicrobial agent.

The antimicrobial agent-containing polyester fiber, etc. thus obtained was scoured, and antimicrobial properties were evaluated. The results are given in Table 3. The antimicrobial properties were evaluated in accordance with a quantitative test of JIS L 1902$^{-1998}$, and the test was carried out using *Staphylococcus aureus*. When the microbiostatic activity was equal to or greater than 2.2, it was evaluated as having antimicrobial properties.

TABLE 3

|  | Filtration pressure increase (kg/cm$^2$) | Filament breakages | Guide wear | Antimicrobial activity |
|---|---|---|---|---|
| Antimicrobial fiber a | 0.2 | None | Small | >5.2 |
| Antimicrobial fiber b | 0.2 | None | Small | >5.2 |
| Antimicrobial fiber c | 1.5 | None | Small | >5.2 |
| Comp. antimicrobial fiber d | 8.3 | None | Medium | >5.2 |
| Comp. antimicrobial fiber e | 4.3 | Once | Medium | >5.2 |
| Comp. antimicrobial fiber f | 22.7 | Three times | Medium | >5.2 |

As is clear from Table 3, the antimicrobial polyester fiber employing the antimicrobial agent of the present invention showed less increase in filter pressure, fewer filament breakages, and little guide wear during spinning, and had excellent processability when fiber spinning. It can also be seen to have high antimicrobial properties.

From these results, the silver-based inorganic antimicrobial agent of the present invention has excellent processability such as spinning properties and also has excellent discoloration resistance when added to a plastic product. Furthermore, it has been confirmed that the silver-based inorganic antimicrobial agent of the present invention has a high antimicrobial effect toward various types of microbes compared with existing silver-based inorganic antimicrobial agents.

INDUSTRIAL APPLICABILITY

Since the novel silver-based inorganic antimicrobial agent of the present invention is a uniform and fine particulate, it has excellent processability and, moreover, it has excellent resistance to discoloration of a plastic product and excellent antimicrobial properties. It is therefore possible to use it as an antimicrobial agent having high suitability in applications where processability is important, such as application to fine fibers, paints, etc.

What is claimed is:

1. A silver-based inorganic antimicrobial agent represented by Formula (1) below $$Ag_aM_bZr_c(PO_4)_3 \cdot nH_2O \qquad (1)$$

in Formula (1), M is at least one type of ion selected from an alkali metal ion, a hydrogen ion, and an ammonium ion, a, b, and c are positive numbers and satisfy 1.5<c<2 and a+b+4c=9, and n is no greater than 2.

2. The silver-based inorganic antimicrobial agent according to claim 1, wherein silver ions are supported on a zirconium phosphate represented by Formula (2) below $$M_{b1}Zr_c(PO_4)_3 \cdot nH_2O \qquad (2)$$

in Formula (2), M is at least one type of ion selected from an alkali metal ion, a hydrogen ion, and an ammonium ion, b1 and c are positive numbers and satisfy $1.5<c<2$ and $b1+4c=9$, and n is no greater than 2.

3. The silver-based inorganic antimicrobial agent according to claim 2, wherein it employs a zirconium phosphate prepared by a wet synthetic method using greater than 1.5 but less than 2 moles of phosphoric acid or a salt thereof relative to 1 mole of a zirconium compound.

4. An antimicrobial product comprising the silver-based inorganic antimicrobial agent according to claim 1.

5. The silver-based inorganic antimicrobial agent according to claim 1, wherein the alkali metal ion is a sodium ion or potassium ion.

6. The silver-based inorganic antimicrobial agent according to claim 1, wherein a is at least 0.01 and no greater than 1.

7. The silver-based inorganic antimicrobial agent according to claim 1, wherein b is at least 0.1 and less than 3.

8. The silver-based inorganic antimicrobial agent according to claim 1, wherein c is greater than 1.75 and less than 1.99.

9. The silver-based inorganic antimicrobial agent according to claim 1, wherein there are more hydrogen ions when comparing alkali metal ions.

10. The silver-based inorganic antimicrobial agent according to claim 1, wherein it has a median diameter of 0.1 to 5 μm.

11. The silver-based inorganic antimicrobial agent according to claim 10, wherein it has a maximum particle diameter of no greater than 10 μm.

12. The silver-based inorganic antimicrobial agent according to claim 10, wherein the standard deviation for the median diameter is no greater than 1.

13. The silver-based inorganic antimicrobial agent according to claim 3, wherein the wet synthetic method is a process in which an aqueous solution comprising a zirconium compound and phosphoric acid or salt thereof is adjusted so as to have a pH of no greater than 4 and then heated at a temperature of at least 70° C.

14. The silver-based inorganic antimicrobial agent according to claim 3, wherein the zirconium compound is at least one selected from the group of zirconium nitrate, zirconium acetate, zirconium sulfate, basic zirconium sulfate, zirconium oxysulfate, and zirconium oxychloride.

15. The silver-based inorganic antimicrobial agent according to claim 3, wherein the phosphoric acid or salt thereof is at least one selected from the group of phosphoric acid, sodium phosphate, potassium phosphate, and ammonium phosphate.

* * * * *